(12) United States Patent
Brookhart et al.

(10) Patent No.: US 10,167,090 B2
(45) Date of Patent: Jan. 1, 2019

(54) SYSTEMS AND METHODS FOR FATIGUE MONITORING

(71) Applicant: Sikorsky Aircraft Corporation, Stratford, CT (US)

(72) Inventors: Andrew Brookhart, Wallingford, CT (US); Raymond J. Beale, Jr., Stratford, CT (US); Matthew Harrigan, Horseheads, NY (US)

(73) Assignee: SIKORSKY AIRCRAFT CORPORATION, Stratford, CT (US)

( * ) Notice: Subject to any disclaimer, the term of this patent is extended or adjusted under 35 U.S.C. 154(b) by 65 days.

(21) Appl. No.: 15/359,667

(22) Filed: Nov. 23, 2016

(65) Prior Publication Data

US 2017/0144778 A1    May 25, 2017

Related U.S. Application Data

(60) Provisional application No. 62/259,951, filed on Nov. 25, 2015.

(51) Int. Cl.
| | | |
|---|---|---|
| *B64D 45/00* | (2006.01) | |
| *B64F 5/00* | (2017.01) | |
| *G01M 17/00* | (2006.01) | |
| *G01N 3/02* | (2006.01) | |
| *G07C 5/08* | (2006.01) | |
| *G01M 5/00* | (2006.01) | |

(52) U.S. Cl.
CPC ............ *B64D 45/00* (2013.01); *B64F 5/0045* (2013.01); *G01M 5/0033* (2013.01); *G01M 17/00* (2013.01); *G01N 3/02* (2013.01); *G07C 5/085* (2013.01); *G07C 5/0808* (2013.01); *B64D 2045/0085* (2013.01)

(58) Field of Classification Search
CPC . B64D 2045/0085; B64F 5/40; G01M 5/0033
See application file for complete search history.

(56) References Cited

U.S. PATENT DOCUMENTS

| | | |
|---|---|---|
| 6,289,289 B1 | 9/2001 | Zweifel |
| 7,532,988 B2 | 5/2009 | Khibnik et al. |
| 7,953,559 B2 | 5/2011 | Sundermeyer et al. |
| 8,571,814 B2 | 10/2013 | Zhao et al. |
| 8,744,651 B2 | 6/2014 | Bates et al. |

(Continued)

FOREIGN PATENT DOCUMENTS

| | | |
|---|---|---|
| EP | 2725337 A1 | 4/2014 |
| WO | WO-2013/191594 A1 | 12/2013 |

OTHER PUBLICATIONS

Extended European Search Report dated Mar. 24, 2017 in connection with co-pending EP Application No. 16200309.9.

*Primary Examiner* — Anshul Sood
(74) *Attorney, Agent, or Firm* — Cantor Colburn LLP

(57) ABSTRACT

A method of monitoring usage to determine accumulated component fatigue damage includes evaluating available data for calculating an accumulated component fatigue damage for a component over a pre-determined time frame. The method includes determining at least one available method for calculating the accumulated component fatigue damage based on the available data. The method includes determining the accumulated component fatigue damage for the component using the at least one available method.

19 Claims, 5 Drawing Sheets

(56) References Cited

U.S. PATENT DOCUMENTS

| | | |
|---|---|---|
| 8,868,284 B2 | 10/2014 | Isom et al. |
| 2003/0083827 A1* | 5/2003 | Chow ...................... F02C 9/52 |
| | | 702/34 |
| 2008/0107518 A1 | 5/2008 | Bode et al. |
| 2009/0306909 A1* | 12/2009 | Mattes ................ G01M 5/0016 |
| | | 702/36 |
| 2012/0031193 A1 | 2/2012 | Adams et al. |
| 2013/0275059 A1 | 10/2013 | Bernhard et al. |
| 2017/0017736 A1 | 1/2017 | Beale et al. |

* cited by examiner

SYSTEMS AND METHODS FOR FATIGUE MONITORING

CROSS REFERENCE TO RELATED APPLICATIONS

This application claims the benefit of priority of U.S. Provisional Patent Application No. 62/259,951, filed Nov. 25, 2015. The contents of which are hereby incorporated herein by reference.

STATEMENT REGARDING FEDERALLY SPONSORED RESEARCH OR DEVELOPMENT

This invention was made with government support under prime contract number W911W6-10-2-0006 awarded by the U.S. Army Aviation Applied Technology Directorate. The government has certain rights in the invention.

BACKGROUND OF THE INVENTION

1. Field of the Invention

The present disclosure relates to fatigue damage due to accumulated loading, and more particularly to systems and methods for aircraft fatigue monitoring.

2. Description of Related Art

Structures such as air vehicles, and particularly rotorcraft structures, are susceptible to accumulated fatigue damage and subsequent fatigue cracking from repetitive loading cycles over the course of the vehicle's service life. Traditional methods to protect against fatigue cracking include assigning a component retirement time or inspection interval based on aircraft utilization rates, for example, using flight hours and/or total take-off and landing cycles. This method requires conservative assumptions about how the aircraft is used in order to ensure a sufficiently low likelihood, e.g. risk, of failure due to fatigue cracking. Due to these conservative assumptions, the frequency of component retirement or inspection in many cases ends up being more than necessary for a given aircraft in view of the actual fatigue damage, usage or loading history of the vehicle.

Such conventional methods and systems have generally been considered satisfactory for their intended purpose. However, there is still a need in the art for improved methods and systems for aircraft fatigue monitoring. The present disclosure provides a solution for this need.

SUMMARY OF THE INVENTION

A method of monitoring loads to determine accumulated component fatigue damage includes evaluating available data for calculating an accumulated component fatigue damage for a component over a pre-determined time frame. The method includes determining at least one available method for calculating the accumulated component fatigue damage based on the available data. The method includes determining the accumulated component fatigue damage for the component using the at least one available method.

The method can include saving the accumulated component fatigue damage for the component during the pre-determined time frame. The available methods to calculate accumulated component fatigue damage can include a loads-based method, a load-regime hybrid method, and/or a regime-based method. The loads-based method can include retrieving load signal data for low-cycle fatigue and high-cycle fatigue from a database for the component during the pre-determined time frame, and calculating accumulated component fatigue damage based on the load signal data.

The load-regime hybrid method can include retrieving load signal data for one of low-cycle fatigue or high-cycle fatigue from a database for the component during the pre-determined time frame, and calculating one of low-cycle fatigue damage or high-cycle fatigue damage based on the load signal data. If the low-cycle fatigue damage is not calculated based on the load signal data, the load-regime hybrid method can include determining the low-cycle fatigue damage for the component during the pre-determined time-frame using a regime history. If the high-cycle fatigue damage is not calculated based on the load signal data, the load-regime hybrid method can include determining the high-cycle fatigue damage for the component during the pre-determined time-frame using the regime history. The load-regime hybrid method can include calculating the accumulated component fatigue damage based on the load signal data and the regime history.

The regime-based method can include determining the low-cycle fatigue damage for the component during the pre-determined time-frame using an regime history. The regime-based method can include determining the high-cycle fatigue damage for the component during the pre-determined time-frame using the regime history. The accumulated component fatigue damage can be calculated based on the low-cycle fatigue damage and the high-cycle fatigue damage that were calculated using the regime history.

When there is more than one available method to calculate accumulated component fatigue damage, the method can include determining the accumulated component fatigue damage by determining the accumulated component fatigue damage using all of the methods to generate multiple accumulated component fatigue damage calculations, and cross-checking the multiple accumulated component fatigue damage calculations with one another to flag inaccurate calculations.

When there is more than one available method to calculate accumulated component fatigue damage, the method can include determining the accumulated component fatigue damage by determining the accumulated component fatigue damage using all of the methods to generate multiple accumulated component fatigue damage calculations. Determining the accumulated component fatigue damage can include selecting one of the available methods based on a pre-determined preferred method. The pre-determined preferred method is dependent on component type.

In accordance with another aspect, a method of monitoring loads to determine component fatigue damage includes retrieving a regime history for a pre-determined time-frame from a database, and determining at least one of a low-cycle fatigue damage and a high-cycle fatigue damage for a component during the pre-determined time-frame using the regime history. The method includes compiling an accumulated damage for the component based on the low-cycle fatigue damage and the high-cycle fatigue damage.

In accordance with some embodiments, determining low-cycle fatigue damage for the pre-determined time-frame includes determining an order of regimes within the regime history. Determining low-cycle fatigue damage for the pre-determined time-frame can include identifying a load order and load magnitude for each regime within the regime history to generate the ordered loads for each regime. Determining the low-cycle fatigue damage can include determining the low-cycle fatigue damage on a maneuver by maneuver basis by cycle counting the ordered loads for each regime within the regime history.

Determining the high-cycle fatigue damage can include calculating the high-cycle fatigue damage for the component using the number of regimes and the regime durations of each regime from the regime history. Determining the high-cycle fatigue damage can include classifying each regime from the regime history as one of a steady regime, a transient regime, or a not-specifically monitored regime. Determining the high-cycle fatigue damage can include assigning a respective damage-per-unit time number to each of the steady regimes, assigning a respective damage-per-event number to each of the transient regimes, and assigning a respective baseline damage-per-unit time number to the not-specifically monitored regimes. Determining the high-cycle fatigue damage can include calculating a fatigue damage for each of the steady regimes by multiplying each respective damage-per-unit time number by the number of time units in each of the respective steady regimes, calculating a fatigue damage for each of the transient regimes by multiplying each respective damage-per-event number by each event of a respective transient regime, and calculating a fatigue damage for each of the not-specifically monitored regimes by multiplying each respective baseline damage-per-unit time number by the number of time units in each of the respective not-specifically monitored regimes.

Determining at least one of the low-cycle fatigue damage or the high-cycle fatigue damage can include pro-rating each regime by gross weight to generate pro-rated regimes. Determining at least one of the low-cycle fatigue damage or the high-cycle fatigue damage can include assigning at least one of a damage number or load magnitude to each pro-rated regime based on flight-test fatigue load data. Determining the total fatigue damage for an air vehicle can include determining the number of a ground-air-ground cycles within the regime history and assigning a fatigue damage number to each ground-air-ground cycle based on the ground-air-ground damage rate.

A system for monitoring usage to determine component fatigue damage includes a load monitoring module having a processor operatively connected to at least one sensor. The processor is configured to perform the method as described above. These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
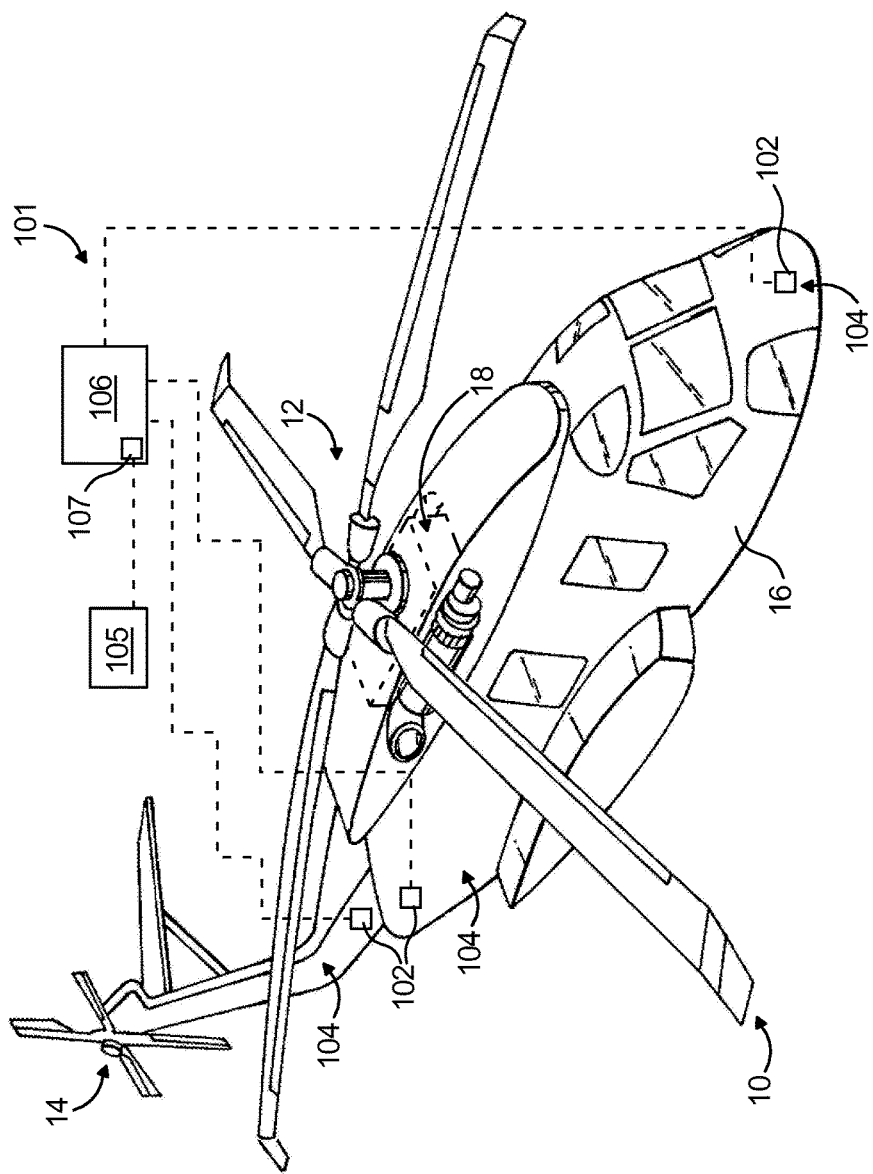
FIG. 1 is a schematic view of an exemplary embodiment of a vertical take-off and landing (VTOL) aircraft, showing a schematic view of an exemplary embodiment of a system for monitoring aircraft usage constructed in accordance with the present disclosure.

Reference will now be made to the drawings wherein like reference numerals identify similar structural features or aspects of the subject disclosure. For purposes of explanation and illustration, and not limitation, a partial view of an exemplary embodiment of a vertical takeoff and landing (VTOL) aircraft in accordance with the disclosure is shown in FIG. 1 and is designated generally by reference character 10. Other embodiments of VTOL aircraft in accordance with the disclosure, or aspects thereof, are provided in FIGS. 2-8, as will be described. The systems and methods described herein provide usage monitoring techniques that allow retirement times and inspection intervals to be extended, while still meeting the same objective risk achieved by traditional methods.

The systems and methods for fatigue monitoring described herein include an improved method for categorizing damaging operating conditions. These improved methods for translating aircraft maneuver history (also known as regime history) into accumulated damage, methods for estimating accumulated damage based on aircraft loads from parametric data (e.g. through load sensors), and for methods determining which accumulated damage calculation to use result in advanced usage and loads monitoring (ULM) that minimizes maintenance burden and costs, while ensuring safety and reliability. The systems and methods described herein can be used for monitoring a variety of components that are susceptible to fatigue damage, for example those found in air vehicles, e.g. aircraft. Aircraft components, such as those found on rotorcraft, can include components which make up the non-rotating portion of the aircraft, or rotor components, e.g. rotating components, sometimes referred to as "dynamic components", with equal applicability. Different components have different sources of fatigue damage, but the damage is grouped into low-cycle fatigue and high-cycle fatigue.

As shown in FIG. 1, VTOL aircraft 10 includes a main rotor system 12 and tail rotor system 14 supported by an airframe 16. Main rotor system includes a main gearbox 18. A system 101 for monitoring aircraft usage includes a load monitoring module 106 having a processor 107 operatively connected to a plurality of load sensors 102 disposed on one or more aircraft components 104 to send load signals to module 106. Processor 107 is operatively connected to a data storage 105, e.g. a memory. It is contemplated that components 104 can be disposed on or integral with airframe 16, or anywhere throughout aircraft 10, internal or external. System 101 can be on aircraft 10 or on the ground. Or, portions of system 101, for example, sensors 102, can be on aircraft 10, while other portions, for example, module 106, processor 107 and/or data storage 105, can be on the ground.

Figure 2:
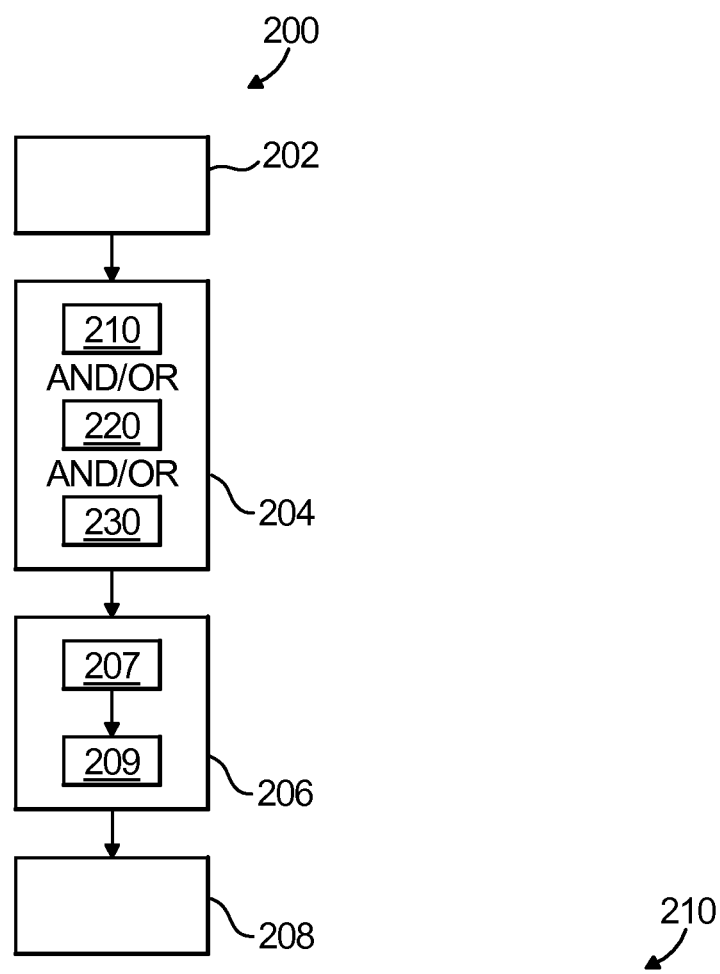
FIG. 2 is a flowchart of an exemplary method for monitoring aircraft component fatigue damage in accordance with an embodiment of the present disclosure, showing operations for determining the accumulated component fatigue damage for an aircraft component.

As shown in FIG. 2, a method 200 of monitoring usage, e.g. aircraft usage, to determine accumulated component fatigue damage includes evaluating available data for calculating an accumulated component fatigue damage for a component, e.g. an aircraft component, over a pre-determined time frame, as indicated by box 202. Method 200 includes determining at least one available method for calculating the accumulated component fatigue damage based on the available data, as indicated by box 204. The available methods to calculate accumulated component fatigue damage include a loads-based method 210, a load-regime hybrid method 220, and/or a regime-based method 230. If both regime data and load signal data are unavailable, those skilled in the art will readily appreciate that the method for calculating the accumulated fatigue damage will be based on the design usage spectrum. The design usage spectrum represents an assumed amount of fatigue damage per-unit time and generally does not take into account actual load data from a load signal or regime-specific load data. A calculation of fatigue damage based on the design usage spectrum is typically the most conservative calculation, e.g. the highest, resulting in more inspections, replacement and/or repair than other methods. The design usage spectrum is the traditional way of determining a load history to compute component fatigue damage.

With continued reference to FIG. 2, method 200 includes determining the accumulated component fatigue damage for the aircraft component using at least one available method, as indicated by box 206. When there is more than one available method to calculate accumulated component fatigue damage, determining the accumulated component fatigue damage includes determining the accumulated component fatigue damage using all of the methods to generate multiple accumulated component fatigue damage calculations, and cross-checking the multiple accumulated component fatigue damage calculations with one another to flag inaccurate calculations, as indicated by box 207.

Determining the accumulated component fatigue damage includes selecting one of the accumulated component fatigue damage calculations based on a pre-determined preferred calculation, as indicated by box 209. The pre-determined preferred calculation is dependent on at least one of aircraft model or component type. Those skilled in the art will readily appreciate that the selected accumulated component fatigue damage is the basis for which the determination to inspect, repair and/or replace components can be made. Method 200 includes saving the accumulated component fatigue damage for the component during the pre-determined time frame, as indicated by box 208. Accumulated component fatigue damage is stored as per-period fatigue damage accumulation for each pre-determined time frame, along with flight hours and methodology type used to compute the fatigue damage assessment.

Figure 3:
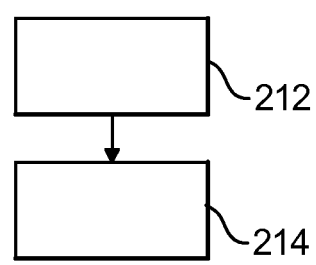
FIG. 3 is a flowchart of another aspect of monitoring aircraft component fatigue damage in accordance with the embodiment of FIG. 2, showing operations for determining the accumulated component fatigue damage using the loads-based method.

As shown in FIG. 3, loads-based method 210 includes retrieving load signal data for low-cycle fatigue and high-cycle fatigue for the aircraft component from a database, e.g. the data storage of system 106, during the pre-determined time frame, as indicated by box 212. The accumulated component fatigue damage is then calculated based on the load signal data, as indicated by box 214.

Figure 4:
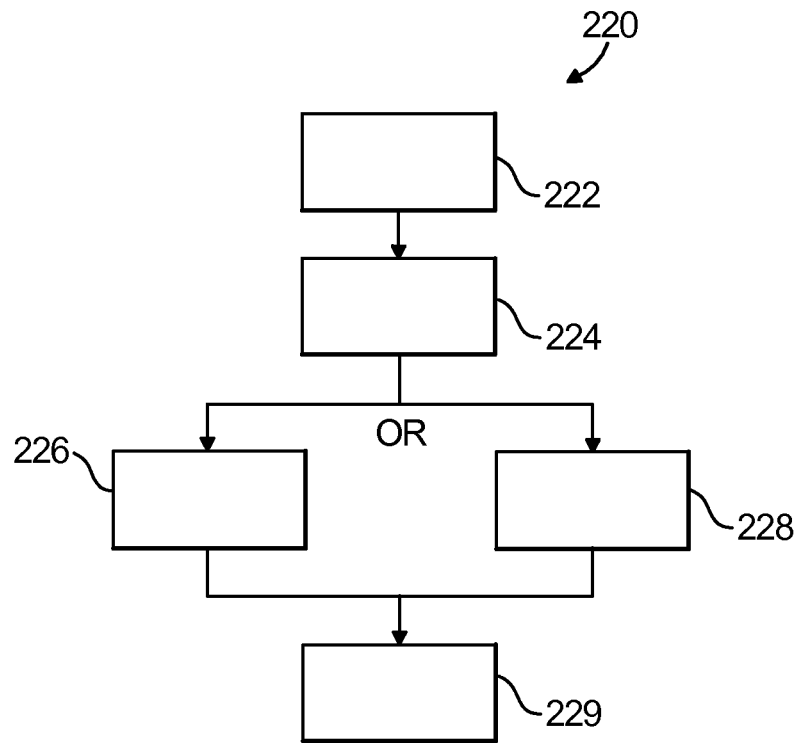
FIG. 4 is a flowchart of another aspect of monitoring aircraft component fatigue damage in accordance with the embodiment of FIG. 2, showing operations for determining the accumulated component fatigue damage using the load-regime hybrid method.

With reference now to FIG. 4, load-regime hybrid method 220 includes retrieving load signal data for one of low-cycle fatigue or high-cycle fatigue from the database for the aircraft component during the pre-determined time frame, as indicated by box 222. One of low-cycle fatigue damage or high-cycle fatigue damage is then calculated based on the load signal data, as indicated by box 224. If the low-cycle fatigue damage is not calculated based on the load signal data, the load-regime hybrid method includes determining the low-cycle fatigue damage for the aircraft component during the pre-determined time-frame using a regime history, e.g. an aircraft regime history, as indicated by box 226. If the high-cycle fatigue damage is not calculated based on the load signal data, the load-regime hybrid method includes determining the high-cycle fatigue damage for the aircraft component during the pre-determined time-frame using the aircraft regime history, as indicated by box 228. The accumulated component fatigue damage is then calculated based on the load signal data and the aircraft regime history, as indicated by box 229.

Figure 5:
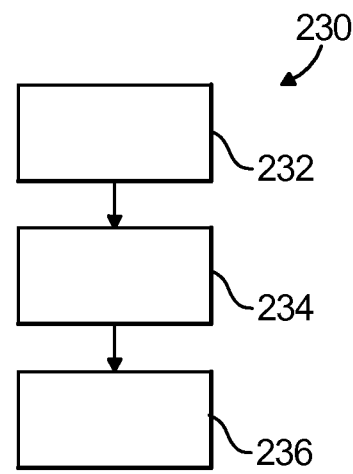
FIG. 5 is a flowchart of another aspect of monitoring aircraft component fatigue damage in accordance with the embodiment of FIG. 2, showing operations for determining the accumulated component fatigue damage using the regime-based method.

As shown in FIG. 5, regime-based method 230 includes determining the low-cycle fatigue damage for the aircraft component during the pre-determined time-frame using an aircraft regime history, as indicated by box 232. Regime-based method 230 includes determining the high-cycle fatigue damage for the aircraft component during the pre-determined time-frame using the aircraft regime history, as indicated by box 234. The accumulated component fatigue damage is then calculated based on the low-cycle fatigue damage and the high-cycle fatigue damage that were calculated using the aircraft regime history, as indicated by box 236.

Figure 6:
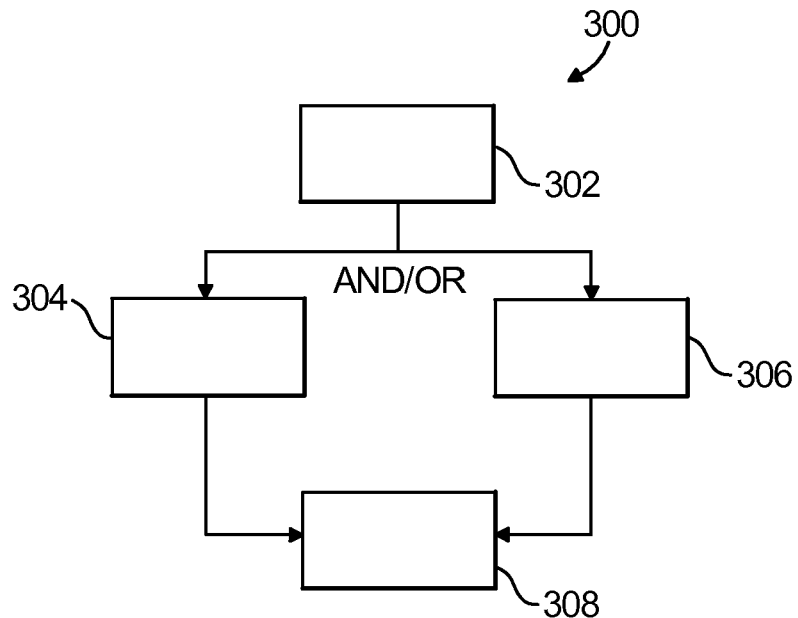
FIG. 6 is a flowchart of another exemplary embodiment for monitoring aircraft component fatigue damage in accordance with an embodiment of the present disclosure, showing operations for determining the accumulated component fatigue damage for an aircraft component.

FIG. 6 is a flow chart of another method 300 for monitoring aircraft usage to determine component fatigue damage in accordance with embodiments of this disclosure. Method 300 includes retrieving an aircraft regime history for a pre-determined time-frame from a database, e.g. the data storage of system 106, as indicated by box 302. The method includes determining a low-cycle fatigue damage and/or a high-cycle fatigue damage for an aircraft component during the pre-determined time-frame using the regime history, as indicated by boxes 304 and 306, respectively. The method includes compiling an accumulated damage for the aircraft component based on the low-cycle fatigue damage and the high-cycle fatigue damage, as indicated by box 308.

Figure 7:
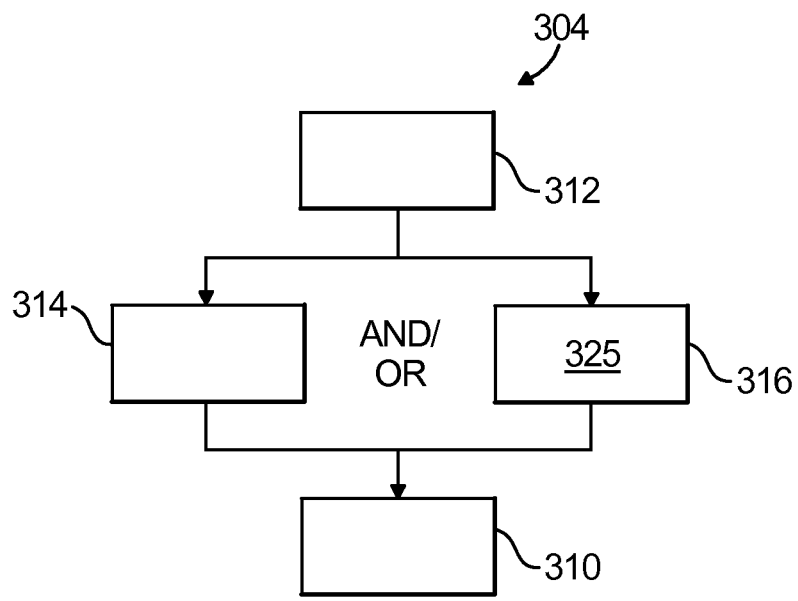
FIG. 7 is a flowchart of another aspect of monitoring aircraft component fatigue damage in accordance with the embodiment of FIG. 6, showing operations for determining the low-cycle fatigue damage.

With reference now to FIG. 7, determining the low-cycle fatigue damage 304 includes determining an order of regimes within the aircraft regime history, as indicated by box 312. If loads data is available for low-cycle fatigue, e.g. through sensors 102, determining low-cycle fatigue damage 304 includes identifying a load order and load magnitude for each regime, e.g. maneuver, within the aircraft regime history to generate the ordered loads for each maneuver, as indicated by box 314. If loads data is not available for low-cycle fatigue, flight-test fatigue load data stored in the database, including minimum and maximum loads and their orders, is used to assign order and load magnitude to each regime occurrence, as indicated by box 316. Determining low-cycle fatigue damage 304 includes determining the low-cycle fatigue damage on a maneuver-by-maneuver basis by cycle counting, for example, rainflow counting, ordered loads for each regime within the aircraft regime history, as indicated by box 310.

In some embodiments, if gross-weight data is available, determining low-cycle fatigue damage for an aircraft component 304 includes pro-rating the low-cycle fatigue load pairs using the gross-weight, as indicated by box 325. Those skilled in the art will readily appreciate that the worst-case load magnitudes acquired during flight-test are split into specific gross-weight bins, e.g. low, medium, and high, or other similar groups. Pro-rating low-cycle fatigue damage by gross weight includes assigning a load magnitude from the gross-weight bins of the database to each regime occurrence based on the gross-weight of the aircraft during that regime occurrence.

Those skilled in the art will readily appreciate that low-cycle fatigue damage includes two regime sub-categories, a Ground-Air-Ground (GAG) cycle and maneuver-to-maneuver loading. The GAG cycle is the combination of the highest load experienced during flight and the lowest load experienced during flight, resulting in a single very large amplitude cycle once per flight. When load signals are available through sensors, e.g. sensors 102, minimum and maximum loads and the associated damage for GAG and for each maneuver are obtained by acquiring the load data from the sensors and performing rainflow counting calculations.

Figure 8:
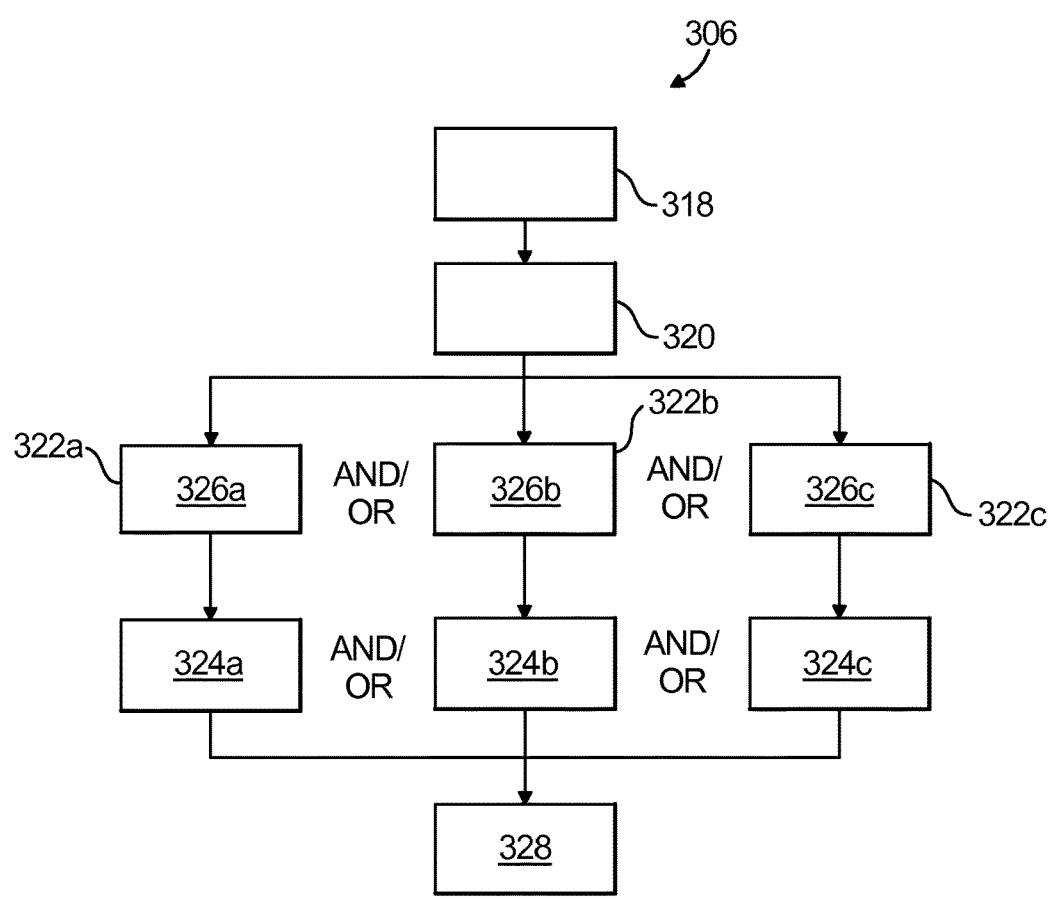
FIG. 8 is a flowchart of another aspect of monitoring aircraft component fatigue damage in accordance with the embodiment of FIG. 6, showing operations for determining the high-cycle fatigue damage.

As shown in FIG. 8, determining the high-cycle fatigue damage 306 includes calculating the high-cycle fatigue damage for the aircraft component using the number of regimes and the regime durations of each regime from the aircraft regime history, as indicated by box 318. Determining the high-cycle fatigue damage 306 includes classifying each regime from the regime history as one of a steady regime, a transient regime, or a not-specifically monitored regime, as indicated by box 320.

With continued reference to FIG. 8, for the monitored regimes, e.g. steady and transient, determining the high-cycle fatigue damage 306 includes assigning a respective damage-per-unit time number to each of the steady regimes, e.g. damage-per-hour or second, as indicated by box 322a, and assigning a respective damage per-event number to each of the transient regimes, as indicated by box 322b. For not-specifically monitored regimes, determining high-cycle fatigue damage includes assigning a baseline damage-per-unit time number according to the design usage spectrum to the not-specifically monitored regimes, also as indicated by box 322c. In some embodiments, if gross-weight data is available, determining high-cycle fatigue damage includes pro-rating the high-cycle damage using the gross-weight data. Pro-rating each regime by gross weight to generate pro-rated regimes includes assigning a damage number, e.g. damage-per-unit time, damage per-event, to each pro-rated regime based on flight-test fatigue load data pro-rated based on gross-weight during flight test, as indicated by boxes 326a-c. The flight-test fatigue load data for high-cycle loads is similarly organized into gross-weight buckets, as described above with respect to low-cycle fatigue damage.

With continued reference to FIG. 8, determining the high-cycle fatigue damage 304 includes calculating fatigue damage for each of the steady regimes by multiplying each respective damage-per-unit time number, either pro-rated or not, by the number of time units in each of the respective steady regimes, as indicated by box 324a. Determining the high-cycle fatigue damage 304 includes calculating fatigue damage for each of the transient regimes by multiplying each respective damage-per-event number, either pro-rated or not, by the number of events in a respective transient regime, as indicated by box 324b. Determining the high-cycle fatigue damage 304 includes calculating fatigue damage for all of the not-specifically monitored regimes by multiplying the respective baseline damage-per-unit time number by the number of time units that the aircraft is in a not-specifically monitored regime, as indicated by box 324c.

Determining the total fatigue damage includes determining the number of GAG cycles within the aircraft regime history and assigning a damage number to each GAG cycle based on the GAG damage rate, as indicated by box 328. Total fatigue damage is finalized by adding the damage numbers due to GAG cycles, not-specifically monitored regimes, transient regimes and steady regimes. Those skilled in the art will readily appreciate that high-cycle fatigue (HCF) damage is generally a result of n/Rev variations in loads, where n is a multiple of the main or tail rotor speed. Generally, these loads are of lower amplitude, but can accumulate very rapidly, due to the high frequency of loading due to rotor harmonics.

The methods and systems of the present disclosure, as described above and shown in the drawings, provide for systems and methods for monitoring usage for system, such as an aircraft, with superior properties including optimization of maintenance, and reduction in maintenance time and costs. While the apparatus and methods of the subject disclosure have been shown and described with reference to preferred embodiments, those skilled in the art will readily appreciate that changes and/or modifications may be made thereto without departing from the spirit and scope of the subject disclosure.

What is claimed is:

1. A method of monitoring usage to determine accumulated component fatigue damage, comprising:
   evaluating, by a processor, available data for calculating an accumulated component fatigue damage for a component over a pre-determined time frame;
   determining, by the processor, at least one available method for calculating the accumulated component fatigue damage based on the available data; and
   determining, by the processor, the accumulated component fatigue damage for the component using the at least one available method; and
   performing maintenance on the component based on the determined accumulated component fatigue damage,
   wherein when the at least one available method is a plurality of available methods, determining the accumulated component fatigue damage includes determining the accumulated component fatigue damage using all of the plurality of available methods to generate multiple accumulated component fatigue damage calculations, and cross-checking the multiple accumulated component fatigue damage calculations with one another to flag inaccurate calculations.

2. The method as recited in claim 1, wherein the at least one available method to calculate accumulated component fatigue damage includes at least one of a loads-based method, a load-regime hybrid method, or a regime-based method.

3. The method as recited in claim 2, wherein the loads-based method comprises:
   retrieving load signal data for low-cycle fatigue and high-cycle fatigue from a database for the component during the pre-determined time frame; and
   calculating accumulated component fatigue damage based on the load signal data.

4. The method as recited in claim 2, wherein the load-regime hybrid method comprises:

retrieving load signal data for one of low-cycle fatigue or high-cycle fatigue from a database for the component during the pre-determined time frame;

calculating one of low-cycle fatigue damage or high-cycle fatigue damage based on the load signal data;

determining the low-cycle fatigue damage for the component during the pre-determined time-frame using a regime history for if the high-cycle fatigue damage has already been calculated, and determining the high-cycle fatigue damage for the component during the pre-determined time-frame using the regime history if the low-cycle fatigue damage has already been calculated; and calculating the accumulated component fatigue damage based on the load signal data and the regime history.

5. The method as recited in claim 2, wherein the regime-based method comprises:

determining a low-cycle fatigue damage for the component during the pre-determined time-frame using a regime history;

determining a high-cycle fatigue damage for the component during the pre-determined time-frame using the regime history; and calculating the accumulated component fatigue damage based on the low-cycle fatigue damage and the high-cycle fatigue damage.

6. The method as recited in claim 1, wherein when the at least one available method includes plurality of available methods, determining the accumulated component fatigue damage includes determining the accumulated component fatigue damage using all of the plurality of available methods to generate multiple accumulated component fatigue damage calculations, and wherein determining the accumulated component fatigue damage includes selecting one of the accumulated component fatigue damage calculations based on a pre-determined preferred calculation, wherein the pre-determined preferred calculation is dependent on the component type.

7. The method as recited in claim 1, further comprising saving the accumulated component fatigue damage for the component during the pre-determined time frame.

8. A method of monitoring usage to determine component fatigue damage, comprising:

retrieving, by a processor, a regime history for a pre-determined time-frame from a database;

determining, by the processor, a low-cycle fatigue damage and a high-cycle fatigue damage for a component during the pre-determined time-frame using the regime history; and compiling, by the processor, an accumulated damage for the component based on the low-cycle fatigue damage and the high-cycle fatigue damage;

performing maintenance on the component based on the determined accumulated component fatigue damage, wherein determining at least one of the low-cycle fatigue damage and the high-cycle fatigue damage includes pro-rating the regime history by gross weight to generate a pro-rated regime history.

9. The method as recited in claim 8, wherein determining low-cycle fatigue damage for the pre-determined time-frame comprises determining an order of regimes within the regime history.

10. The method as recited in claim 8, wherein determining low-cycle fatigue damage for the pre-determined time-frame comprises identifying a load order and load magnitude for each regime within the regime history to generate the ordered loads for each regime, wherein the ordered loads.

11. The method as recited in claim 10, wherein determining the low-cycle fatigue damage comprises determining the low-cycle fatigue damage on a maneuver by maneuver basis by cycle counting ordered loads for each regime within the regime history.

12. The method as recited in claim 8, wherein determining the high-cycle fatigue damage comprises calculating the high-cycle fatigue damage for the component using the number of regimes and the regime durations of each regime from the regime history.

13. The method as recited in claim 8, wherein determining the high-cycle fatigue damage comprises classifying each regime from the regime history as one of a steady regime, a transient regime, or a not-specifically monitored regime.

14. The method as recited in claim 13, wherein determining the high-cycle fatigue damage comprises assigning a respective damage-per-unit time to each of the steady regimes, assigning a respective damage-per-event number to each of the transient regimes, and assigning a baseline damage-per-unit time number according to the design usage spectrum to the not-specifically monitored regimes.

15. The method as recited in claim 14, wherein determining the high-cycle fatigue damage comprises calculating a fatigue damage for each of the steady regimes by multiplying each respective damage-per-unit time number by the number of time units in each of the respective steady regimes, calculating a fatigue damage for each of the transient regimes by multiplying each respective damage-per-event number by the number of events in a respective transient regime, and calculating a fatigue damage for each of the not-specifically monitored regimes by multiplying each respective baseline damage-per-unit time number by the number of time units in each of the respective not-specifically monitored regimes.

16. The method as recited in claim 8, wherein pro-rating the regime history includes assigning at least one of a damage number or a load magnitude to each regime based on flight-test fatigue load data associated with the gross-weight.

17. The method as recited in claim 8, wherein determining a total fatigue damage for an air vehicle includes determining a number of a ground-air-ground cycles within the regime history and assigning a damage number to each ground-air-ground cycle based on ground-air-ground damage rate.

18. The method as recited in claim 8, further comprising storing the accumulated damage for the component during the pre-determined time-frame in a database.

19. A system for monitoring usage to determine component fatigue damage comprising:

a processor;

a memory operatively coupled to the processor, wherein the processor is operable to:

evaluate available data for calculating an accumulated component fatigue damage for a component over a pre-determined time frame;

determine at least one available method for calculating the accumulated component fatigue damage based on the available data; and determine the accumulated component fatigue damage for the component using the at least one available method; and perform maintenance on the component based on the determined accumulated component fatigue damage, wherein when the at least one available method is a plurality of available methods, determining the accumulated component fatigue damage includes determining the accumulated component fatigue damage using all of the plurality of available methods to generate multiple accumulated component fatigue damage calculations, and cross-checking the multiple accumulated component fatigue damage calculations with one another to flag inaccurate calculations.

\* \* \* \* \*